US006368611B1

(12) United States Patent
Whitbourne et al.

(10) Patent No.: US 6,368,611 B1
(45) Date of Patent: Apr. 9, 2002

(54) ANTI-INFECTIVE COVERING FOR PERCUTANEOUS AND VASCULAR ACCESS DEVICE AND COATING METHOD

(75) Inventors: Richard J. Whitbourne, Rochester; Xianping Zhang, Webster, both of NY (US)

(73) Assignee: STS Biopolymers, Inc., Henrietta, NY (US)

( * ) Notice: Subject to any disclaimer, the term of this patent is extended or adjusted under 35 U.S.C. 154(b) by 0 days.

(21) Appl. No.: 09/386,187

(22) Filed: Aug. 31, 1999

(51) Int. Cl.[7] .................................................. A01N 25/34

(52) U.S. Cl. ........................ 424/411; 424/409; 424/422; 424/423; 604/918; 523/122

(58) Field of Search ............................... 424/422–424, 424/10.2, 409, 407, 411, 419; 600/29, 30, 32, 40, 41; 604/890.1, 891.1, 892, 264, 265, 508, 509, 577, 907, 910, 912, 914, 916, 918; 523/122

(56) References Cited

U.S. PATENT DOCUMENTS

| 2,302,933 | A | * | 11/1942 | Barol | 424/10.2 |
|---|---|---|---|---|---|
| 2,898,913 | A | * | 8/1959 | Ritter et al. | 424/423 |
| 3,366,114 | A | * | 1/1968 | Kanter | 424/422 |
| 4,054,139 | A | * | 10/1977 | Crossley | 128/260 |
| 4,677,143 | A | * | 6/1987 | Laurin et al. | 523/122 |
| 5,112,618 | A | | 5/1992 | Cartmell et al. | |
| 5,204,110 | A | | 4/1993 | Cartmell et al. | |
| 5,238,685 | A | | 8/1993 | Wren | |
| 5,260,066 | A | | 11/1993 | Wood et al. | |
| 5,322,695 | A | | 6/1994 | Shah et al. | |

FOREIGN PATENT DOCUMENTS

| DE | 3830359 | * | 12/1939 | | |

OTHER PUBLICATIONS

D.L. Veenstra, et al., "Efficacy of antiseptic–impregnated central venous catheters in preventing catheter–related bloodstream infection: a meta–analysis", *JAMA*, Jan. 20, 1999, 281(3): 261–7.

G.R. Collin, "Decreasing catheter colonization through the use of an antiseptic–impregnated catheter: a continuous quality improvement project", *Chest*, Jun., 1999, 115(6): 1632–40.

A. Bach, et al., "Efficacy of silver–coating central venous catheters in reducing bacterial colonization", *Crit Care Med*, Mar., 1999, 27(3): 515–21.

T.S. Huth, et al., "Clinical trial of injunction seals for the seals for the prevention of urinary catheter–associated bacteriuria", *Arch Intern Med*, Apr. 1992, 152(4): 807–12.

H.K. Butler, et al., "Evaluation of polymyxin catheter lubricant and impregnated catheters", *J Urol*, Oct. 1968, 100(4): 560–6.

C.M. Kunin, et al., "Evaluation of an intraurethral lubricating catheter in prevention of catheter–induced urinary tract infections", *J Urol*, Dec. 1971, 106(6): 928–30.

(List continued on next page.)

*Primary Examiner*—Neil S. Levy
(74) *Attorney, Agent, or Firm*—Kenyon & Kenyon (57) ABSTRACT

A part that can be introduced and/or implanted in the body, in body parts, or in body cavities, made of nonmetallic material or having a nonmetallic surface is designed such that infections associated with the use of parts of this type are reduced or entirely eliminated. This is achieved due to the fact that the entire surface of this part or parts or, depending on the effect, partial areas of this part or parts, that are nevertheless not in geometric contact, is/are furnished with a metallization (6). It is also possible that the material at least in the area of its exterior surface (17) contains metallic particles (18) in powder or granular form made of a metal having an oligodynamic effect, and that the most exterior metallic particles (18) are uncovered at least partially at the surface.

29 Claims, 1 Drawing Sheet

OTHER PUBLICATIONS

H. Liedberg, et al., "Silver coating of urinary catheters prevents adherence and growth of Pseudomonas aeruginosa", *Urol Res*, (1989), 17(6):357–8.

H. Liedberg, et al., "Assessment of silver–coated urinary catheter toxicity by cell culture", *Urol Res*, (1989), 17(6): 359–60.

J.R. Johnson, et al., "Prevention of catheter–associated urinary tract infection with a silver oxide–coated urinary catheter: clinical and microbiologic correlates", *J Infect Dis*, Nov. 1990, 162(5): 1145–50.

* cited by examiner

ANTI-INFECTIVE COVERING FOR PERCUTANEOUS AND VASCULAR ACCESS DEVICE AND COATING METHOD

The present invention relates to a part that can be introduced and/or implanted in the body, in body parts, or in body cavities, in accordance with the preamble of Claim 1 and of Subclaim 2.

A part of this type in the form of a catheter is known, for example, from German Laid-Open Print 35 16 830. There, the treatment segment of the catheter is provided with a metallized area. This metallized area aids in supplying electrical power for achieving a therapeutic or operative effect through heat.

An electrically conductive area provided in the treatment area of a heat applicator is also known from German Laid-Open Print 33 15 303. When it is used as a catheter, this part is designed so as to be flexible, and the outer layer, i.e., the external conductor, is coated with Teflon to produce a thick, smooth surface.

In plastic parts of this type or parts that are coated using plastic, such as short-term catheters, e.g., heart catheters or long-term catheters, e.g., cava catheters, pacemaker probes, heart valve tissues, hydrocephalus drainages, bladder catheters, nourishment catheters, dialysis catheters, drainage catheters for septic wounds, resuscitation tubes, surgical thread material, or the like, so-called plastic infections often occur as a result of bacterial colonies on the plastic parts, or parts having a plastic surface, that are introduced into the body, body parts or body cavities. It is generally known that bacteria on plastics or plastic surfaces of this type often encounter favorable conditions for life. Thus, for example, bacteria are transported by the blood to the plastic parts, where they can establish themselves, actively adhering, and can increase rapidly due to the favorable conditions for life. As a result, serious infectious diseases can arise.

The objective of the present invention is therefore to indicate a possibility by which infections of this type can be reduced or completely eliminated through the use of parts of this type.

In accordance with the invention, this objective is achieved by the features indicated in the characterizing part of Claim 1 or of Subclaim 2.

According to the present invention, the plastic part, or the plastic surface of a part of this type, is provided entirely or partially with a metallization, for example, by a continuous metal coating or one made up of individual areas, or by introducing into the non-metallic material metal particles, e.g., in powder and/or granular form.

The aforementioned bacteria can not only not adhere to and thrive on this metallization, but they are killed off, presumably as a result of the formation of metal ions, which usually represent a powerful poison for bacteria. As a result, bacterial colonies are avoided in the area of the introduced and/or implanted parts made of non-metallic material, in particular plastic, or having a nonmetallic surface, especially a plastic surface.

Figure 1:
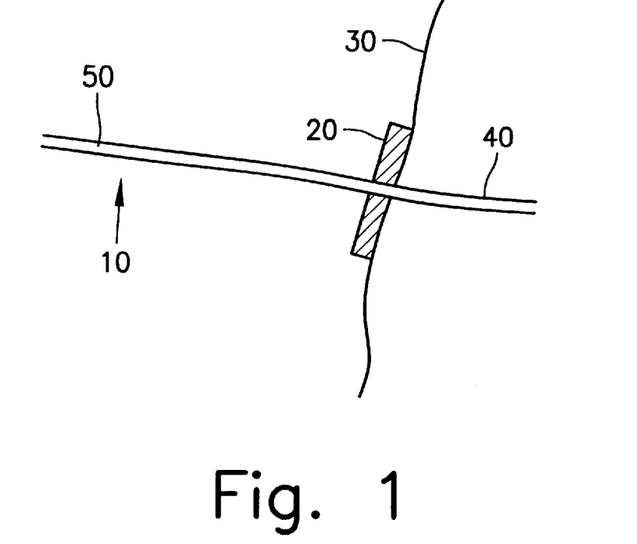
FIG. 1 is a side view of a kit of the invention.
Figure 2:
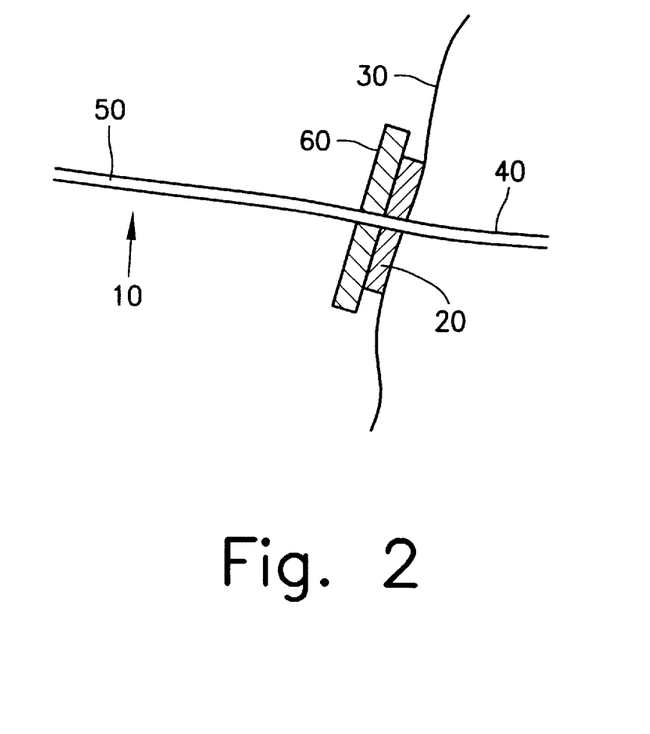
FIG. 2 is a side view of a second embodiment of a kit of the invention.

Further advantageous details and refinements of the present invention are indicated in the subclaims and will be described in greater detail below on the basis of the exemplary embodiments illustrated in the drawing:

FIG. 1 depicts the front section of a balloon catheter, partially in a cutaway view, FIG. 2 depicts a segment of a plastic part, partially in a cutaway view, FIG. 3 depicts an enlarged top view of the surface of a plastic wall or plastic surface covered only partially by a metallic coating, FIG. 4 depicts a venous indwelling cannula in a [side] view, FIG. 5 depicts a cross-section of a cannula having metallic particles embedded in the area of the exterior surface coating, FIG. 6 depicts a cross-section of a cannula having metallic particles embedded in the area of the exterior and interior surface coating, and FIG. 7 depicts a cross-section of a cannula having metallic particles distributed homogeneously in the non-metallic material.

In FIG. 1, a plastic part that can be introduced or implanted into the body or body parts is designated using reference numeral 1 and in the exemplary embodiment is configured as a balloon catheter. It is composed of a plastic tube 2, on which in the front part in treatment area 3 an inflatable balloon 5 is provided. Balloon catheters of this type are generally known.

According to the present invention, wall 4 of plastic tube 2 and balloon wall 5' is provided with a metallization 6 in the form of a metallic coating. In this context, the metal used can be one that demonstrates an increased oligodynamic effect. By oligodynamic effect is meant the sterilizing effect of metal ions in liquids. The latter are generally powerful poisons for bacteria. Particularly well-suited for this purpose is silver or copper or an alloy composed of both. However, other metals such as iron, high-grade steel, tin, aluminum, nickel, or alloys of two or more of these metals, including silver and copper, can be used successfully, the one or the other metal demonstrating a lesser or greater oligodynamic effect depending on the bacteria type.

Metallization 6 can advantageously be applied using vacuum vapor deposition or chemical deposition, e.g., through the reduction of metal complexes or through cathode atomization, or the like.

It is also possible, as FIG. 2 indicates, in one of the aforementioned manners or in a different manner, e.g., by brushing on tin-chloride or palladium chloride, etc., to initially apply an electrically conductive base layer 7 on plastic wall 4 or, e.g., on a plastic layer covering a flexible metallic hose. Subsequently, desired metallization 6 is applied using electroplating or chemical deposition.

Metallization 6 or base layer 7 do not necessarily have to constitute a homogeneous continuous coating. Rather, it is sufficient if the plastic wall or its exterior surface is seeded with metals or metal alloys having an oligodynamic effect.

Seeding is understood as only a partial coating in the form of individual zones 8 that are not in contact with each other. This is represented in FIG. 3 as a surface segment. A metallization of this type can in itself suffice to achieve the desired effect. A metallization of this type, however, can also be subsequently strengthened, e.g., using a generally known chemical method, using vacuum deposition, or the like. Base layer 7 can also be produced by vacuum deposition or chemically. In the event of subsequent reinforcement, the base layer does not have to be composed of a metal that demonstrates an oligodynamic effect. For example, it is also possible that the surface of the plastic be composed only of a thin coating, which, by way of example, can be tin chloride or palladium chloride.

Metallization 6 applied on base layer 7 then is composed of one of the aforementioned metals or metal alloys.

In FIG. 4, a venous indwelling cannula 8 is depicted in whose catheter 9 composed of an elastic plastic a steel cannula 10 is inserted, whose tip 11 somewhat protrudes from catheter 9 in a familiar manner. Connected to catheter 9 is a mouthpiece 12, that passes over into a tube 13. On tube 13, a support 14 is arranged which can be locked by a cap 15. Support 14 acts as a connecting armature for further medical and/or other devices, e.g., syringes, three-way valves, or the like.

Cannula grip 16 is attached at end 13' of tube 13. On tube 13, there are also arranged lateral brackets 17. These act to secure the cannula on the body, e.g., using a bandage and/or using an adhesive strip.

According to the present invention, at least catheter 9, but preferably also mouthpiece 12, are furnished with the oligodynamic metallic coating of the aforementioned type. If appropriate, venous indwelling cannula 8 made entirely of plastic can be furnished with a coating of this type on its entire surface. The elasticity of catheter 9 will in no way be impaired by the metallic coating applied.

According to another type of embodiment of the present invention, in place of the metallization of the nonmetallic material, a metallic powder or a metallic granulate can be arranged so as to be distributed in the nonmetallic material such that at least on the exterior surface, for example of a catheter or of another kind of cannula, partial areas of metallic particles can be exposed and they can promote the desired oligodynamic effect. This occurs advantageously when this part is manufactured in extrusion, injection, or injection molding processes.

In most cases, it will be sufficient that, in accordance with FIG. 5, metallic particles 18 are furnished in the area of exterior surface 17 of wall 4 made of nonmetallic material, such as in a catheter. Of these particles, the most exterior ones are partially exposed so that they can promote the oligodynamic effect.

As is illustrated in FIG. 6, plastic tube 2, preferably a catheter, can be provided with metallic particles 18 also in the area of interior surface 19, the metallic particles being partially exposed on the interior and exterior surfaces.

According to the production process, the simplest arrangement seems to be the one in FIG. 7. In this exemplary embodiment, metallic particles 18 are distributed in the nonmetallic material homogeneously or at least approximately homogeneously.

The production of these exemplary embodiments depicted in FIGS. 5 through 7 is advantageously achieved using an extrusion, injection molding, or transfer molding process, i.e., in a thermoplastic process. As a material for nonmetallic wall 4 or the like, a thermoplast is preferably used. Suited for this purpose are polycarbonates, halogenized hydrocarbons, polyamides, polyacrylics, polyimides, polyurethane, etc., or mixtures thereof.

Metallic particles 18 can be provided in powder form, having a large or small scatter range of the particle size, also having varying particle sizes, and/or as granulate, and/or as microspheres.

In an advantageous manner, the metallic particles can also be made of a metallic mixture of two elements situated as far apart as possible from each other in the electrochemical series. In addition, more than two metals or alloys can be considered for use.

According to one advantageous refinement of the present invention, exterior surface 17 and, if appropriate, also interior surface 19 can be roughened. In this manner, the proportion of the exposed metallic particles 18 can be significantly increased. The roughening can be achieved mechanically and/or chemically.

In particular, the surface(s) can receive a chemical surface treatment, for example using an etching chemical agent, as a result of which the plastic content on surface(s) is reduced and, as a result, the percentage of metallic particles 18 on the surface (s) is correspondingly increased.

A particularly high concentration of an exposed metallic particle surface is obtained through the use of microspheres as metallic particles 18 and in response to the subsequent roughening of surface (s) 17, 19, since, as a result, the shell of, e.g., hollow microspheres is destroyed and therefore the greater interior surface of the latter is exposed.

The present invention can be used especially advantageously in short-term catheters and in drainages.

What is claimed is:

1. A kit comprising:
   an insertable medical device having a percutaneously insertable surface; and
   a disc provided with an antimicrobial composition, said composition comprising at least one antimicrobial agent exhibiting antimicrobial activity when in a substantially dry state or when solvated after being in a substantially dry state, said disc surrounding and abutting said percutaneously insertable surface when a portion of said percutaneously insertable surface projects from an external bodily surface, and said disc is in contact with said external bodily surface.

2. A part that can be introduced and/or implanted in the body, in body parts, or in body cavities, optionally including parts that are connected thereto such as connecting elements leading to the outside, or the like, made of nonmetallic material or having a nonmetallic surface, characterized in that the material at least in the area of its exterior surface (17) contains metallic particles (18) in powder and/or granulate form made of metal having an oligodynamic effect, and that the metallic particles closest to the surface are uncovered at least partially at the surface.

3. The part as recited in claim 1, characterized in that the metallization (6) is made of a metal or a metal alloy having an oligodynamic effect.

4. The part as recited in claim 1 or 3, characterized in that the metallization (6) is made of a continuous, electrically conductive coating.

5. The part as recited in claim 1 or 3, characterized in that the metallization (6) is made of individual zones (8), not in contact geometrically with each other, that are composed of an electrically conductive coating.

6. The kit of claim 1, wherein said anti-infective composition comprises an antimicrobial agent and a corticosteroid.

7. The part as recited in one of claims 1 or 3 through 6, characterized in that the metallization (6) is applied using vacuum vapor deposition.

8. The part as recited in one of claims 1 or 3 through 6, characterized in that the metallization (6) is applied using a chemical process.

9. The part as recited in one of claims 1 or 3 through 8, characterized in that the metallization (6) is reinforced using electroplating or by chemical means.

10. The part as recited in one of claims 1 or 3 through 9, characterized in that an electrically conductive base layer (7) is provided, on which the metallization (6) is applied.

11. The part as recited in claim 9 or 10, characterized in that the reinforcement of the metallization, or the metallization (6) applied to the conductive base layer (7), is made of a different metal or of a different metal alloy—or contains it or them—from the base layer (7).

12. The part as recited in claim 2, characterized in that the metal particles (18) are furnished in the form of microspheres.

13. The part as recited in claim 2 or 12, characterized in that the surface is roughened.

14. The part as recited in claim 2, 12, or 13, characterized in that the metal particles (18) are distributed homogeneously in the nonmetallic material.

15. The part as recited in one of claims 1 through 14, characterized in that the nonmetallic material is made of a thermoplastically deformable plastic.

16. The part as recited in claim 15, characterized in that the nonmetallic material is made of at least one of the plastics, polyurethane, polyamide, polyimide, polyacrylic, polycarbonate, polyhalogen hydrocarbon, or mixtures of them.

17. The part as recited in one of claims 2 or 12 through 16, characterized in that the metallic particles are made of one or more of the metals existing as mixture and/or alloy, silver, copper, iron, tin, zinc, high-grade steel, aluminum, or nickel.

18. The part as recited in one of claims 1 through 17, characterized in that it is composed of a plastic catheter (9), a mouthpiece (12) connected thereto, and one or more connecting device or devices (14) mounted on it, and that at least the catheter (9) and the mouthpiece (12) are metallized, or at least a surface (17) or the surfaces (17 and 19) have exposed segments of metal particles (18).

19. A method for manufacturing a part corresponding to one of claims 2 or 12 through 18, characterized in that the surface layer (17) or the surface layers (17 and 19) or the homogeneous distribution of metallic particles (18) or the material having the homogeneously distributed metallic particles (18) are produced using an extrusion process.

20. The method as recited in claim 19, characterized in that the layer or layers is/are applied using an extrusion process, in that the uncoated tubular part is guided essentially by a nozzle and, in this context, a plastic mixed with the metal, on the exterior and optionally also on the interior, is applied in an injection and/or a molding process.

21. The method as recited in claim 20, characterized in that the surface(s) of the applied layer(s) is/are roughened.

22. The method as recited in claim 21, characterized in that the surface(s) is/are mechanically roughened.

23. Th e method as recited in claim 21, characterized in that the surface(s) is/are chemically roughened.

24. The method as recited in claim 23, characterized in that the surface(s) receive a chemical surface treatment, as a result of which the plastic content on the surface(s) is reduced and, as a result, the metallic particles (18) constitute a correspondingly greater proportion in the surface(s).

25. The method as recited in one of claims 19 through 24, characterized in that, as a plastic, a thermoplast is used.

26. The method as recited in one of claims 19 through 25, characterized in that, as a plastic, one of the materials, polyurethane, polyamide, polyacrylic, or mixtures of them is/are used.

27. The method as recited in one of claims 19 through 26, characterized in that the metal is used in the form of microspheres.

28. The method as recited in one of claims 19 through 27, characterized in that, as metal for the metallic particles (18), one of the metals, silver, copper, iron, tin, zinc, high-grade steel, aluminum, or nickel, or mixtures of two or more of these metals or their alloys, optionally having metallic particles (18) made of one metal, is/are used.

29. A kit comprising:

an insertable medical device, with a percutaneously insertable surface, wherein said surface is provided with an anti-infective coating; and a disc provided with an antimicrobial composition, said composition comprising at least one antimicrobial agent exhibiting antimicrobial activity when in a substantially dry state or when solvated after being in a substantially dry state, said disc surrounding and abutting said percutaneously insertable surface when a portion of said percutaneously insertable surface projects from an external bodily surface, and said disc is in contact with said external bodily surface.

* * * * *

UNITED STATES PATENT AND TRADEMARK OFFICE
CERTIFICATE OF CORRECTION

PATENT NO. : 6,368,611 B1
DATED : April 9, 2002
INVENTOR(S) : Richard J. Whithourne It is certified that error appears in the above-identified patent and that said Letters Patent is hereby corrected as shown below:

Delete Columns 1-6 and substitute therefore Columns 1-10 as shown on the attached pages Signed and Sealed this Ninth Day of December, 2003

JAMES E. ROGAN
*Director of the United States Patent and Trademark Office*

ANTI-INFECTIVE COVERING FOR PERCUTANEOUS AND VASCULAR ACCESS DEVICE AND COATING METHOD

FIELD OF THE INVENTION

The present invention relates to a kit comprising an insertable or implantable medical device for use in combination with a disc, having anti-infective properties capable of reducing the incidence and/or severity of infections occurring at or associated with the site of insertion on the bodily surface of such devices.

BACKGROUND OF THE INVENTION

Insertable or implantable medical devices include, but are not limited to needles, infusion sets, peripheral venous catheters and needles, central venous catheters, arterial catheters, epidural and spinal catheters, dialysis catheters, percutaneous nephrostomy and cystostomy tubes. Before such devices are used, for example, to introduce various materials such as nutrients or therapeutic agents into patients, or to drain material from a patient, they must be inserted into the patient's body. In the course of placing a device, contamination can occur, as individuals often proceed in an ad hoc fashion. Typically, when a needle or catheter is inserted, the area of insertion is cleaned with an antiseptic. For example, this can be done by wiping the area with a swab saturated with 70% alcohol. Often, the site will be palpated after swabbing, occasionally contaminating the site.

When such devices are left in place, even for a few days, infections often result. Exudate often seeps from the insertion site. The exudate picks up skin flora which can diffuse back into the patient along the wetted device surface, thereby causing infection.

Many investigators have tried to solve this problem. For example, placement of a junction seal after placement of a urinary catheter has been examined for preventing bacteriuria and reducing mortality. In one study, the incidence of bacteriuria was higher in a control group than in a treatment group for some of the potential risk factors studied, yet the differences were not statistically significant. (T. S. Huth, Arch. Intern. Med. 152:807, 1992). Lubricants containing polymyxin B or placebo were used with catheters impregnated with tetramethylthyuramdisulfide and a cyclic thiohydroxamic proprietary agent and no significant difference between these types of catheters and catheter care was seen (H. K. I. Butler, J. Urol. 100:560, 1968). Catheters designed for instillation of intraurethral antibacterial lubricants also were not efficacious in reducing the incidence of infections. (C. M. Kunin, J. Urol. 106:928, 1971). Further, initial reports that silver coating of catheters prevented the adherence and growth of *Escherichia coli* and *Pseudomonas aeroginosa* in vitro without causing cell toxicity, led to the use of silver oxide urinary catheters. (H. Liedberg, Urol. Res. 17:357, 1989; H. Liedberg, Urol. Res. 17:359, 1989). However, a large clinical trial of silver oxide coated urinary catheters in selected patients yielded similar rates of infection between the silver coated group and the uncoated control silicone catheter group. (J. R. Johnson, J. Infect. Dis. 162:1145, 1990). Coated central venous catheters demonstrated a lower catheter colonization rate than observed in uncoated controls. (Veentra, JAMA 281:261, 1999; Collins, Chest 115:1632, 1999). In contrast, other studies reported no benefit to the use of coated central venous catheters. (Bach, Crit. Care Med. 27:515 1999).

Some wound healing products contain films or hydrogel layers which may be wetted with liquid materials to promote wound healing. For example, hydrogel wound dressing products are described in U.S. Pat. Nos. 5,204,110, and 5,112,618. Examples of bandages for wound dressings which contain therapeutic agents are described in U.S. Pat. Nos. 5,260,066 and 5,322,695. However, such products are not suitable for limiting infection at the insertion site of an insertable or implantable medical device.

Hence, there remains a need for a method and products for limiting the degree of contamination, including preventing or reducing the growth of microorganisms within an exudate, at the insertion site of an insertable or implantable medical device.

SUMMARY OF THE INVENTION

The present invention provides a kit useful for preventing or inhibiting the development of infections arising from insertion or implantation of a medical device through a bodily surface. The kit comprises an insertable medical device and a disc. The device has a portion that can be inserted or implanted into the body. Part of, or the entire surface of, the portion of the device that can be inserted or implanted into the body is coated with an anti-infective coating.

The disc can be used with any insertable medical device. The disc can be provided with anti-microbial properties by being coated or saturated with an antimicrobial composition. According to the invention, a preferred composition comprises at least one antimicrobial agent capable of exhibiting antimicrobial activity when essentially dry or when solvated after being essentially dry.

The disc preferably is capable of being penetrated by the device. Alternatively, the disc can be placed around the device. In use, the disc should be in contact with the body surface and surrounds and abuts the portion of the insertable portion of the device that projects from the surface of the body.

Another aspect of this invention provides a kit comprising a medical device and disc, as well as a swab, wetted with an anti-infective coating solution. The swab preferably is used to coat the insertable portion of the device, before the device is placed into the body. The kit of the invention can also include an absorbent pad wetted with an antimicrobial composition. The insertable medical device can be placed into subcutaneous tissue, a peripheral vein, a central vein, an artery, a physiologic body cavity or a pathologic cavity.

The disc can have a sufficient amount of adhesive on one surface to adhere the disc to the body surface and can be flexible, porous and/or absorbent. Examples of materials that the disc can be composed of are polypropylene, polyethylene, and woven materials composed of polyester, rayon or cotton.

In one embodiment of the invention, the disc comprises at least two layers. A first layer can be placed against the body surface, and preferably is permeable to the antimicrobial agent. A second layer preferably contains an antimicrobial agent in a solvated or dry form, such that the antimicrobial agent can permeate through the first layer.

The invention includes a method of inhibiting or reducing the incidence of infection associated with inserting a medical device in a patient, wherein an insertable surface of said device is coated, at least in part, with an anti-infective coating, which comprises inserting the device in a patient such that a portion of an inserted surface of the device projects from a bodily surface. A disc is contacted with the bodily surface where the device projects from the bodily surface such that said disc surrounds and abuts the inserted surface projecting from the bodily surface, wherein the disc is coated or saturated with an antimicrobial composition. The composition comprises at least one antimicrobial agent capable of exhibiting antimicrobial activity when in a substantially dry state or when solvated after being in a substantially dry state.

DETAILED DESCRIPTION OF THE PREFERRED EMBODIMENTS

Referring to FIG. 1, the invention is directed to a kit comprising an insertable medical device 10 and a disc 20. The insertable medical device 10 is capable of penetrating or passing through a body surface 30. The device comprises a distal portion 40 that is capable of being inserted or implanted into the body and a proximal portion 50 that remains outside the body. Sites within the body that can be accessed by the device include but are not limited to vascular and subcutaneous sites, body cavities, potential spaces, and pathologic cavities. The device includes but is not limited to infusion devices, such as peripheral venous catheters and indwelling infusion needles, such as butterfly needles, subcutaneous access devices such as those used with insulin pumps and patient controlled analgesia (PCA) pumps, arterial catheters, central venous catheters, dialysis catheters, including peritoneal dialysis catheters, nephrostomy catheters, percutaneous cystostomy catheters, indwelling paracentesis and pleurocentesis catheters and drains, and spinal and epidural catheters.

The outer surface of the distal portion 50 of the insertable medical device preferably is coated with an anti-infective coating, partially or over its entire surface. Optionally, the proximal portion 40 of the device also can be coated with the anti-infective coating.

The anti-infective coating is capable of reducing or eliminating any contamination that occurs during the introduction of the device into the body and has antiseptic, antibiotic, disinfectant, antiviral, and/or antifungal properties. The anti-infective coatings include, but are not limited to, those described below and the anti-infective coatings described in U.S. Pat. Nos. 5,069,899 and 5,525,348, each of which are incorporated in their entirety herein by reference. In one embodiment of the invention, a swab wetted with the anti-infective coating optionally is provided so that the device can be coated by wiping the device with the swab and allowing it to dry before insertion.

The disc 20 is substantially planar and is composed of an absorbent or non-absorbent material, preferably, an absorbent material. Examples of appropriate materials include, but are not limited to, plastic foams, cotton gauzes, or porous filter material, polypropylene film, polyethylene film, and woven materials composed of polyester, rayon or cotton. As used herein, the term disc includes an object having a surface capable of contacting a bodily surface, regardless of the actual shape. In practice the disc 20 can be circular, rectangular, or any other suitable shape. Hence, the disc 20 is of a shape and size appropriate to the type of medical device and the location where the device 10 is placed. For example, a larger bore access device may require a larger disc 20 than a smaller bore device. A circular disc 20 with a diameter of approximately 2.5 cm can be used for a small needle device. A peritoneal dialysis catheter may require a substantially larger disc 20 measuring up to 15 cm in size and preferably rectangular in shape.

As shown in FIG. 2, another embodiment of the present invention comprises an absorbent pad 60 used in combination with a coated disc 20 to form the disc. The coated disc 20 preferably is composed of a flexible inert material. Suitable materials include but are not limited to polypropylene film and polyethylene film, woven materials composed of polyester, rayon and cotton. The coated disc 20 can be rendered permeable by the presence of a multitude of fine perforations. The fine holes permit easier penetration of the disc 20 by the insertable portion of the device 10. The holes allow access of the solution contained within the disc 20 to the body surface 30, and also allow drainage of any exudate or transudate from the body surface entry site, which can solvate the dried anti-infective composition permitting it to exert its anti-infective properties at the site where the insertable medical device 10 enters the body. The absorbent pad 60 is composed of a material capable of absorbing or being soaked or wetted by the antimicrobial composition. Examples of appropriate materials include, but are not limited to, plastic foams, cotton gauzes, or porous filter material.

The disc 20 has an anti-infective coating. The coating is applied to one or both sides of the disc 20 and allowed to dry, so that the disc 20 preferably is dry when applied to the skin. In the preferred embodiment of the present invention, the disc 20 is of approximately the same size and shape as the absorbent pad 60. However, the absorbent pad 60 and coated disc 20 also can have different sizes and shapes. Optionally, the disc and pad may be adhered to one another. In addition, the disc 20 may be provided with an adhesive material at one surface which permits the disc to adhere to the body surface 30. In use, the disc 20 preferably contacts the body surface 30. The absorbent pad 60 preferably contacts the disc 20, separated from the body surface 30 by the coated disc 20. If only one side of the disc is coated with antimicrobial composition, the coated side preferably is placed against the body surface 30. The system is secured to the skin with an adhesive material such as adhesive tape.

The disc 20 can be coated, impregnated or saturated or otherwise provided with an antimicrobial composition with antiseptic, antibiotic, disinfectant, antiviral, and/or antifungal properties. An amount of antimicrobial solution is provided to the disc, which is sufficient to provide an effective amount of the antimicrobial agent, and which preferably is sufficient to render the disc substantially wet when used.

Suitable antimicrobial compositions useful in the invention include solutions of bacteriocides, antibiotics, antifungal agents, antiviral agents, and/or antiseptics that are suitable for human use. Suitable agents include, but are not limited to 2-bromo-2-nitropropane-1,3-diol (sold under the trade name Bronopol®), polyhexanide (sold under the trade name Cosmocil CQ®), and benzalkonium chloride. Suitable solvents include those that are compatible with the bacteriocides, antibiotics, antifungal agents, antiviral agents, and/or antiseptics, and appropriate for human use. Preferred solvents include, but are not limited to one, or preferably more than one of the following, ethanol, saline solution, more preferably Normal saline solution, tetrahydrofuran, and benzyl alcohol. Preferably, glycerine or polyethylene glycol (PEG), more preferably PEG 400 is a component of the composition. Other suitable solvents can be used.

In one embodiment of the invention, corticosteroids are included in the antimicrobial composition. Suitable corticosteroids, include synthetic and natural corticosteroids. In a preferred embodiment dexamethasone is used. Other suitable corticosteroids include, but are not limited to, alclometasone dipropionate, amcinonide, betamethasone, clobetasol proprionate, clocortolone pivalate, cortisone, hydrocortisone, desonide, desoximetasone, diflorasone diacetate, fluocinolone acetonide, fluocinonide, fluandrenolide, halcinonide, methylprednisolone, mometasone furoate, and triamcinolone.

The antimicrobial composition used with the disc 20 preferably contains a polyurethane resin, more preferably 2% to 10% by weight polyurethane resin, most preferably 4% to 6% by weight polyurethane resin. A preferred solvent, ethanol, preferably contains 1% to 10% by weight nitrocellulose, and more preferably also contains 2% to 4% polyurethane resin. Preferred antimicrobial agents include, but are not limited to, benzalkonium chloride and/or 2-bromo-2-nitropropane-1,3-diol. A preferred embodiment of the present invention employs an antimicrobial composition comprising nitrocellulose in ethanol, tetrahydrofuran, and benzyl alcohol in a ratio of 2:15:1 by weight, with polyurethane resin, more preferably about 5% polyurethane resin, and preferably 0.2% to 1.0% of one or more of the antimicrobial agents, most preferably 0.5% of the antimicrobial agent or agents. The disc can be coated with the composition and then can be dried by heating, such as by heating in an oven at about 40° C. to 60° C., most preferably at about 50° C.

The disc 20 preferably surrounds and abuts the insertable portion of the device 10 at a position on device 10 where a portion of the device 10 projects from the body surface 30. In one embodiment of the invention, the disc 20 is placed onto the body surface 30 and the insertable portion of the device is then passed through the disc 20 into the body. In another embodiment, the insertable portion of the device is passed through the center of the disc 20, and is then inserted into the body. In a third embodiment, the kit is packaged with the disc 20 already in place on the device 10. In another embodiment of the present invention the disc 20 has an opening or slit extending from a radially interior portion to its edge. In this embodiment, the disc 20 is placed on the body surface 30, around the device 10 after the device 10 has been inserted into the body.

The disc 20 preferably is wet when applied to body surface 30 and when the device 10 is inserted into the body. The disc 20 then is permitted to dry, leaving the anti-infective material in or on the disc 20. If an exudate develops at the access site, it can absorbed by the disc 20. The exudate can solubilize or solvate the anti-infective material, which can exert an anti-infective effect at the site, limiting or preventing infection. In one embodiment of the invention, only the disc 20 is supplied for use with the medical access device 10 of the user's choice. Optionally, a swab wetted with the anti-infective coating can be supplied for coating the selected medical access device.

The examples listed below are illustrative and are not intended to limit the scope of the invention.

EXAMPLE 1

Anti-Infective Solutions

The solutions used in the Examples 2 to 5 are as follows:

| Solution A | |
| --- | --- |
| PEG 400 | 3 gm |
| Ethanol | 12 gm |
| 2-bromo-2-nitropropane-1,3-diol | 0.05 gm |
| Polyhexanide | 0.25 gm |
| Dexamethasone | 0.03 gm |
| Solution B | |
| PEG 400 | 4.4 gm |
| Ethanol | 19.2 gm |
| 0.9% saline | 18 gm |
| Sodium chloride | 0.27 gm |
| 2-bromo-2-nitropropane-1,3-diol | 0.15 gm |
| Polyhexanide | 0.75 gm |
| Dexamethasone | 0.12 gm |

5BRON
0.5% 2-bromo-2-nitropropane-1,3-diol and 5% polyurethane resin in: 3% nitrocellulose in a solvent of ethanol, tetrahydrofuran, and benzyl alcohol 2/15/1 by weight 5BAK
0.5% benzalkonium chloride and 5% polyurethane resin in: 3% nitrocellulose in a solvent of ethanol, tetrahydrofuran, and benzyl alcohol, in a ratio of 2:15:1, by weight

| 1BRON | |
| --- | --- |
| PEG 400 | 12 gm |
| Ethanol | 48 gm |
| 2-bromo-2-nitropropane-1,3-diol | 0.4 gm |

BRONBAK
0.5% 2-bromo-2-nitropropane-1,3-diol, 0.5% Benzalkonium chloride, and 5% polyurethane resin, in 3% nitrocellulose in ethanol, tetrahydrofuran and benzyl alcohol 2/15/1 by weight

EXAMPLE 2

Method for Making Discs

An anti-infective disc was made by manually coating a 0.0005" thick polypropylene sheet with about 3 ml of 5BRON. The sheet then was dried in an oven at 50° C. for 60 minutes for each coated side. Discs of 2.5 cm diameter were cut from the coated sheet. Other discs coated with 5BAK and with BRONBAK were made from sheets of 0.0005" thick polypropylene in a similar manner, except that 5BAK and BRONBAK were substituted for 5BRON.

EXAMPLE 3

Method of Using 5BRON Coated Disc

A Clinipad® alcohol wipe was dried out and saturated with Solution A. A butterfly needle (PolyfinQQ® Ref-365 bent needle) was coated with Solution A using a cotton tipped swab and air dried for a few minutes. A disc coated with 5BRON was placed over an insertion site of a human subject. An alcohol wipe saturated with Solution B was placed over the disc. Thereafter, the coated, bent needle was inserted through the alcohol wipe and disc into subcutaneous tissue. The needle was secured using dressing tape. The needle was removed aseptically using sterile gloves 7 days after insertion. On gross physical examination, the needle site did not appear to be infected. After removal, the needle tip was cut using sterile cutters and dropped into a tube containing Phosphate Buffer with Tween 80. The buffer was vortexed for 30–45 seconds. A sterile swab was used to streak three Standard Method Agar (SMA) plates, which were then streaked for isolation. The plates were incubated for 5 to 7 days at 37±2° C. Resulting colonies were identified, and moderate growth of gram positive cocci and gram negative coccobacilli was reported from the cultured needle tip.

EXAMPLE 4

Method for Using 1BRON and 5BAK Solutions

A MiniMed®MMT-365 infusion set was placed as described below. An alcohol wipe was allowed to dry, and saturated with 1BRON by placing the wipe in a vessel containing 1BRON. An insertion site for a human subject was wiped with a second alcohol wipe. A polypropylene disc coated was coated with 5BAK, allowed to dry, and was placed on the insertion site. Thereafter, the alcohol wipe saturated with the 1BRON solution was placed over the disc on the insertion site. Next, the bent needle was swabbed with 1BRON solution, inserted through the alcohol wipe saturated with 1BRON solution, through the disc, into the skin, and secured in place using surgical adhesive tape. After 5 days in place, the needle was removed. The site was clean and did not appear to be infected.

EXAMPLE 5

Use of BRONBAK Solution and Culture Results

A. BRONBAK Studies

BRONBAK coated discs were used in tests that were conducted as described in Example 3. A dried alcohol swab saturated with Solution B and a needle coated with Solution A were used. The needle tip was cultured for bacteria after removal, as described in Example 3. The results of the cultures are shown in Table 1.

TABLE 1

Bacterial Culture Results of Needle Tips after Use of Invention

| Test Number | Days inserted | Disc Coating | Culture Results |
| --- | --- | --- | --- |
| 1 | 7 | 5BRON | No Growth |
| 2 | 7 | BRONBAK | No Growth |
| 3 | 6 | BRONBAK | Light Growth |
| 4 | 5 | BRONBAK | No Growth |
| 5 | 9 | BRONBAK | No Growth |

B. Control Experiments

Additional control experiments were conducted in which the anti-infective technology of the instant invention was not used. Instead, needle insertion was conducted following the practice generally described above. The results are shown in Table 2.

TABLE 2

Bacterial Culture Results of Needle Tips Without Use of Invention

| Test Number | Days inserted | Disc Coating | Gauze Coating | Needle Coating | Needle Tip Culture |
| --- | --- | --- | --- | --- | --- |
| 6 | 2 | No Disc | No Gauze | None | No Growth |
| 7 | 2 | No Disc | No Gauze | None | No Growth |
| 8 | 3 | No Disc | No Gauze | None | No Growth |
| 9 | 3 | No Disc | No Gauze | None | No Growth |

An additional control experiment was conducted in which needle insertion was conducted following practice generally as described above. A site on the left side of the anterior abdomen was wiped with an alcohol soaked pad (Clinipad® alcohol wipe). Then a butterfly needle (Minimed Polyfin QQ® with wings infusion Set Ref, MMF-365) was placed through the skin into the subcutaneous tissue, and the site was covered with sterile dressing tape. After four days the site had become infected, and the needle had to be removed.

We claim:

1. A kit comprising:
   an insertable medical device having a percutaneously insertable surface; and
   a disc provided with an antimicrobial composition, said composition comprising at least one antimicrobial agent exhibiting antimicrobial activity when in a substantially dry state or when solvated after being in a substantially dry state, said disc surrounding and abutting said percutaneously insertable surface when a portion of said percutaneously insertable surface projects from an external bodily surface, and said disc is in contact with said external bodily surface.

2. The kit of claim 1, further comprising a swab with an anti-infective solution for providing said implantable surface with an anti-infective coating before said device is inserted.

3. The kit of claim 1, further comprising an absorbent pad saturated with an antimicrobial composition comprising at least one antimicrobial agent exhibiting antimicrobial activity when in a substantially dry state or when solvated after being in a substantially dry state, said pad surrounding and abutting said insertable surface while said pad is in contact with said disc.

4. The kit of claim 1, wherein said device is constructed and arranged for insertion into a vehicle selected from the group consisting of subcutaneous tissue, a peripheral vein, a central vein, an artery, a physiologic body space or a pathologic space.

5. The kit of claim 1, wherein said disc is provide with a sufficient amount of an adhesive to adhere said disc to said bodily surface.

6. The kit of claim 1, wherein said anti-infective composition comprises an antimicrobial agent and a corticosteroid.

7. The kit of claim 6, wherein said anti-infective composition comprises a polyethylene glycol; 2-bromo-2-nitropropane-1,3-diol; polyhexanide; and dexamethasone.

8. The kit of claim 1, wherein said antimicrobial composition comprises a polyurethane resin, nitrocellulose in ethanol, tetrahydrofuran, benzyl alcohol, and an antimicrobial agent.

9. The kit of claim 8, wherein said antimicrobial agent is selected from the group consisting of an antiseptic, antibiotic, disinfectant, antiviral agent, antifungal agent, and mixtures thereof.

10. The kit of claim 1, wherein said antimicrobial composition contains one or more agents selected from the group consisting of 2-bromo-2-nitropropane-1,3-diol, benzalkonium chloride, polyhexanide, bacitracin, neomycin, silver sulfadiazine, AgCl, and chlorhexidine.

11. The kit of claim 10, wherein said antimicrobial agent is selected from the group consisting of 2-bromo-2-nitropropane-1,3-diol and benzalkonium chloride.

12. The kit of claim 1, wherein said antimicrobial composition comprises polyethylene glycol 400 in an amount from about 15% to about 25% w/w; ethanol in an amount from about 70% to about 85% w/w; dexamethasone in an amount from about 1% to about 3% w/w; 2-bromo-2-nitropropane-1,3-diol in an amount from about 0.30% to about 0.40% w/w; and polyhexanide in an amount from about 1.5% to about 2.0%.

13. The kit of claim 1, wherein said antimicrobial composition comprises polyethylene glycol; ethanol; a corticosteroid; 2-bromo-2-nitropropane-1,3-diol; polyhexanide; and a saline solution.

14. The kit of claim 13, wherein said antimicrobial composition comprises polyethylene glycol 400 in an amount from about 8% to about 12% w/w; ethanol in an amount from about 40% to about 50% w/w; Normal saline in an amount from about 35% to about 45%; dexamethasone in an amount from about 0.2% to about 0.3% w/w; 2-bromo-2-nitropropane-1,3-diol in an amount from about 0.30% to about 0.40% w/w; and polyhexanide in an amount from about 1.5% to about 2.0%.

15. The kit of claim 1, wherein said antimicrobial composition comprises a polyurethane resin; nitrocellulose in ethanol; tetrahydrofuran; benzyl alcohol; and a substance chosen from the group consisting of 2-bromo-2-nitropropane-1,3-diol and polyhexanide.

16. The kit of claim 15, wherein said antimicrobial composition comprises: 2-bromo-2-nitropropane-1,3-diol in an amount from about 0.1% to about 2.0% w/w; polyurethane resin in an amount from about 3% to about 7% w/w; from about 2% to about 4% by volume nitrocellulose in ethanol, in an amount from about 7% to about 12% w/w; tetrahydrofuran in an amount from about 80% to about 90% w/w; and benzyl alcohol in an amount from about 4% to about 6% w/w.

17. The kit of claim 1, wherein said antimicrobial composition comprises: benzalkonium chloride in an amount from about 0.1% to about 2.0% w/w; polyurethane resin in an amount from about 3% to about 7% w/w; from about 2% to about 4% by volume nitrocellulose in ethanol, in an amount from about 7% to about 12% w/w; tetrahydrofuran in an amount from about 80% to about 90% w/w; and benzyl alcohol in an amount from about 4% to about 6% w/w.

18. The kit of claim 1, wherein said disc is permeable.

19. The kit of claim 1, wherein said disc is made of an absorbent material.

20. The kit of claim 1, wherein said disc is composed of a material selected from the group consisting of polypropylene, polyethylene, and woven materials selected from the group consisting of polyester, rayon and cotton.

21. The kit of claim 1, wherein said disc comprises a permeable layer adapted to be placed adjacent to a bodily surface, and a second layer containing an antimicrobial agent capable of permeating into and through said first layer.

22. A method of inhibiting the incidence of infection associated with insertion of a medical device in a patient, which method comprises:
  inserting said device in a patient such that a portion of said device projects from a bodily surface; and
  contacting a disc with said device where said device projects from said bodily surface such that said disc surrounds and abuts said insertable device projecting from said bodily surface, wherein said disc is provided with an antimicrobial composition, said composition comprising at least one antimicrobial agent capable of exhibiting antimicrobial activity when in a substantially dry state or when solvated after being in a substantially dry state.

23. The method of claim 22, wherein said device penetrates said disc prior to being inserted into said patient.

24. The method of claim 22, wherein said device is provided with an anti-infective coating containing one or more agents selected from the group consisting of 2-bromo-2-nitropropane-1,3-diol, benzalkoniun chloride, polyhexanide, bacitracin, neomycin, silver sulfadiazine, AgCl, and chlorhexidine.

25. The method of claim 24, wherein said antimicrobial composition provided with said disc contains one or more agents selected from the group consisting of 2-bromo-2-nitropropane-1,3-diol, benzalkonium chloride, polyhexanide, bacitracin, neomycin, silver sulfadiazine, AgCl, and chlorhexidine.

26. The method of claim 25, wherein said antimicrobial composition comprises: 2-bromo-2-nitropropane-1,3-diol in an amount from about 0.1% to about 2.0% w/w; polyurethane resin in an amount from about 3% to about 7% w/w; from about 2% to about 4% by volume nitrocellulose in ethanol, in an amount from about 7% to about 12% w/w; tetrahydrofuran in an amount from about 80% to about 90% w/w; and, benzyl alcohol in an amount from about 4% to about 6% w/w.

27. The method of claim 24, wherein said antimicrobial composition comprises: benzalkonium chloride in an amount from about 0.1% to about 2.0% w/w; polyurethane resin in an amount from about 3% to about 7% w/w; in a concentration from about 2% to about 4% nitrocellulose in ethanol in an amount from about 7% to about 12% w/w; tetrahydrofuran in an amount from about 80% to about 90% w/w; and benzyl alcohol in an amount from about 4% to about 6% w/w.

28. A device comprising:
  a disc provided with an antimicrobial composition, said composition comprising at least one antimicrobial agent exhibiting antimicrobial activity when in a substantially dry state or when solvated after being in a substantially dry state; and,
  said disc surrounding and abutting an inserted surface of an insertable medical device, when a portion of said inserted surface projects from a bodily surface, and said disc is in contact with said bodily surface.

29. A kit comprising:
  an insertable medical device, with a percutaneously insertable surface, wherein said surface is provided with an anti-infective coating; and
  a disc provided with an antimicrobial composition, said composition comprising at least one antimicrobial agent exhibiting antimicrobial activity when in a substantially dry state or when solvated after being in a substantially dry state, said disc surrounding and abutting said percutaneously insertable surface when a portion of said percutaneously insertable surface projects from an external bodily surface, and said disc is in contact with said external bodily surface.

* * * * *